United States Patent [19]

Malkemus et al.

[11] 4,159,389

[45] Jun. 26, 1979

[54] PROCESS FOR THE PRODUCTION OF DICUMYL PEROXIDE

[75] Inventors: John D. Malkemus; Yun G. Chang, both of Austin, Tex.

[73] Assignee: Reichhold Chemicals, Inc., White Plains, N.Y.

[21] Appl. No.: 906,586

[22] Filed: May 16, 1978

[51] Int. Cl.$^2$ .......................................... C07C 179/04
[52] U.S. Cl. ..................................................... 568/562
[58] Field of Search .................... 260/610 A, 610 B; 568/562, 576

[56] References Cited

U.S. PATENT DOCUMENTS

| | | | |
|---|---|---|---|
| 2,668,180 | 2/1954 | Boardman et al. | 260/610 R |
| 2,691,683 | 10/1954 | Lorand et al. | 260/610 R |
| 3,310,588 | 3/1967 | Kloosterman et al. | 260/610 R |
| 3,829,503 | 8/1974 | Kato | 260/610 R |

FOREIGN PATENT DOCUMENTS

| | | | |
|---|---|---|---|
| 954361 | 4/1964 | United Kingdom | 260/610 R |
| 1243313 | 8/1971 | United Kingdom | 260/610 R |

*Primary Examiner*—Werren B. Lone

[57] ABSTRACT

This invention relates to an improved method for the production of high purity dicumyl peroxide. As produced, dicumyl peroxide contains many impurities which must be removed. Generally, our invention comprises flash distilling crude dicumyl peroxide, separating and discarding the distillate and allowing the residual product to crystallize. The supernatant liquid from the crystallized dicumyl peroxide is then fed into the next batch of crude dicumyl peroxide to be distilled. In this manner high yields are obtained along with a very rapid distillation time. Because the supernatant liquid from each crystallization is fed back into the process, the dicumyl peroxide normally left in the supernatant is recovered in the subsequent steps.

1 Claim, No Drawings

PROCESS FOR THE PRODUCTION OF DICUMYL PEROXIDE

PRIOR ART

This invention generally applies to the art of making and purifying peroxides and, in particular, dicumyl peroxide. The following literature references and patents are related:

1. Tijssen, Stephanus B., Koninklijke Industrieele Maatschappij voorheen Noury & Van der Lande, "Improvements in or Relating to Ditertiary Peroxides", British Pat. No. 954,361, Apr. 8, 1964.
2. Tijssen, Stephanus B., Koninklijke Industrieele Maatschappij voorheen Noury & Van der Lande, "Process for the Crosslinking of Polyolefins and for the Vulcanization of Rubber", U.S. Pat. No. 3,267,066.
3. Tijssen, Stephanus B., Koninklijke Industrieele Maatschappij, "Process for Crosslinking of Copolymers of Ethylene or for the Vulcanization of Natural and Synthetic Rubber", German Patent Offenlegungsschrift No. 1,494,143, Jan. 16, 1969.
4. Koninklijke Industrieele Maatschappij Noury & Van der Lande N.V., "Process for the Preparation of New Organic Peroxides", Netherland No. 7013105, Jan. 25, 1971.
5. Bafford, Richard A.; Mageli, Orville L.; Pennwalt Corporation, "Organic Peroxides", British Pat. No. 1,243,313, Aug. 18, 1971.
6. Bafford, Richard A.; Mageli, Orville L.; Pennwalt Corporation, "Process for the Preparation and Purification of Organic Peroxides", German Patent Offenlegungsschrift No. 2,016,108, Oct. 21, 1971.
7. Kato, M.; Komai, T.; Aoshima, K.; Nippon Oil and Fats Company, Ltd., "Process for Producing Organic Peroxides", U.S. Pat. No. 3,829,503, Aug. 13, 1974.
8. Kato, M.; Komai, T.; Aoshima, K.; Japan Oil and Fats Company, Ltd., "Tertiary Peroxides", German Patent Offenlegungsschrift No. 2,035,127, Oct. 28, 1971.
9. Koninklijke Industrieele Maatschappij N. V. voorheens Noory & Van de Lande N. V., "Dicumyl Peroxide and Ring-chlorinated Derivatives", Belgian Pat. No. 619,409, Oct. 15, 1962.
10. Brown, Herbert C. and Rei, M., "A Convenient Procedure for the Quantitative Conversion of Reactive Alcohols and Olefins into the Corresponding Chlorides", J. Organic Chemistry, 31, 1090-93 (1966).
11. The following U.S. Pat. Nos.: 2,668,180, 3,254,130, 3,310,588 and 2,691,683.

BACKGROUND OF THE INVENTION

High purity dicumyl peroxide is used as a catalyst in a variety of chemical reactions. One of the most important uses of dicumyl peroxide is as a cross-linking agent for polyethylene compounds such as those used for wire in cable coating. In addition, dicumyl peroxide is also used for cross-linking ethylene-vinyl acetate copolymer compounds. In order to be suitable for these uses, the dicumyl peroxide must be of a very high purity, at least 90%, and free from contaminants and by-products of production.

Crude dicumyl peroxide has been prepared by various methods. These methods generally comprise reacting cumene hydroperoxide with either cumyl alcohol or alpha-methyl styrene. Since most, if not all, of the commercial methods employ the use of acidic type catalysts, the crude dicumyl peroxide contains impurities such as acetone, phenol, acetophenone and unreacted cumyl alcohol or alpha-methyl styrene. Since it is not practical to purify the cumene hydroperoxide starting material above about 80 to 85%, the cumene hydroperoxide itself contains not only unreacted cumene but also some relatively high boiling impurities. These include cumyl alcohol, acetophenone and other materials which are carried over into the dicumyl peroxide.

Prior art, which is exemplified by British Pat. No. 1,243,313, teaches that acetone and phenol may be removed from crude dicumyl peroxide by first extracting the material with an aqueous sodium hydroxide solution and followed by washing with water to remove the alkaline solution. The final washed product may then be purified by several methods which include crystallization and recrystallization, heating under vacuum to remove the volatile impurities and a partial steam distillation under vacuum. The latter method, under reduced pressure, is a much better method of removing the volatile impurities.

Both of the above distillation methods of removing the volatile impurities; that is, the vacuum distillation in the absence and in the presence of added water, have been evaluated and both do, in fact, remove some of the volatile impurities. However, both methods have significant disadvantages. The principal disadvantage of the vacuum distillation in the absence of water is that a vacuum in the order of one millimeter of mercury is required at a temperature of about 90° to 100° C. for a prolonged period of time in order to produce a product of acceptable purity, i.e. at least 90%. Although this method may be accomplished batch-wise in the laboratory, there is extreme inherent danger in heating large amounts of dicumyl peroxide at such an elevated temperature. Since dicumyl peroxide is not thermally stable, some decomposition occurs during this long heating process.

British Pat. No. 1,243,313 states that "the other method" (other than crystallization) "for purifying crude dicumyl peroxide consists of distilling impurities by heating the crude peroxide at 90° to 110° C. under high vacuum for several hours. The hazards of heating peroxides at these temperatures and the necessity of a high vacuum make this process commercially unattractive. This distillation can give a product assaying about 90% but it has a dark amber color and must be decolorized and recrystallized to be acceptable commercially; also these products may go off color in ordinary storage". From this patent, and from our own laboratory work, it became obvious that an improved method for purifying dicumyl peroxide was needed in order to rapidly produce a high purity product for commercial use.

We have now discovered an improved method that will rapidly purify crude dicumyl peroxide. The dicumyl peroxide obtained from our process not only is high in purity, 90 to 95±%, but is also light in color. Our process allows for both batch-wise and continuous process of the product with equal purity.

DETAILED DESCRIPTION OF THE INVENTION

Initial work was performed according to the above-mentioned British Patent. This process did produce a light-colored product. However, the product was wet with water and in order to be used, this water must be removed. Further, relatively large amounts of water are required to be co-distilled with the volatile impurities so that a much longer time is needed as compared with our simple one-pass distillation. The British prior art also discloses that crude dicumyl peroxide may be purified by cooling to approximately −10° C., allowing crystallization to occur. However, this procedure gives an oily solid which, in turn, must be recrystallized from a solvent such as methanol. In addition, unless the crude dicumyl peroxide contains at least 75% dicumyl peroxide, crystallization will not take place. Thus, relatively high purity crude dicumyl peroxide is needed as a starting material. In contradistinction, our invention is applicable to crude dicumyl peroxide containing quantities of dicumyl peroxide below 75%. In fact, when the dicumyl peroxide content is low in the crude product, it is even more economical than the prior art since the supernatant liquid recovered from the crystallization contains relatively large amounts of dicumyl peroxide which would be extremely hard to recover. By our process, this large quantity of supernatant liquid is added to the next batch of crude dicumyl peroxide and the product is recovered as part of the next batch.

We have discovered that high purity dicumyl peroxide may be produced in good yield by simply flash distilling the crude product once under vacuum. The distillate is discarded, while the product from which the distillate was removed is allowed to crystallize at or slightly below room temperature, i.e. from about 20° C. to about −10° C. Once the dicumyl peroxide crystallizes out, the mother liquid or the supernatant is removed. It may be removed by decanting, filtration or centrifuging. The novelty of this invention accrues from the fact that the mother liquid or supernatant is then added back to the next run to repeat the process over again. This procedure results in increased yields of pure, above 90%, dicumyl peroxide in the next and following runs.

Quite simply, the process of our invention consists of preparing crude dicumyl peroxide by any of the methods known in the art. This crude dicumyl peroxide is washed several times with dilute sodium hydroxide solution and then once with dilute sodium sulfite solution. After that, the crude material is washed with sodium sulfate solution containing a small amount of mineral acid. The washed crude dicumyl peroxide is ready for purification which may be either batch-wise or continuous.

In the batch-wise procedure, the washed crude dicumyl peroxide is placed in a distillation apparatus. The temperature is raised between 85° and 100° C. and vacuum is applied. The vacuum should be as low as possible, between 0.1 and 10 millimeters and preferably between 1 and 5 millimeters of mercury, absolute. At these temperatures and pressures, the volatiles are rapidly removed from the crude dicumyl peroxide. Distillation time will vary depending on the vacuum applied and the temperature. Experience will establish the proper time, but it will generally be in the range of 5 to 15 minutes and up to several hours if large quantities of crude dicumyl peroxide are used. At this point, the distillate is discarded and the prepurified dicumyl peroxide is removed from the distillation apparatus and allowed to crystallize. The supernatant liquid is removed from the crystalline product and placed back into the distillation apparatus along with additional washed crude dicumyl peroxide of the next batch. The resulting mixture is then distilled as previously described and the process is repeated over and over.

In a continuous process, which is preferred, the washed crude dicumyl peroxide is fed along with previously recovered supernatant liquid into a commercial continuous distillation apparatus. As before, the distillate is discarded, while the prepurified dicumyl peroxide is recovered in a separate, cooled vessel. The supernatant liquid, which is continuously formed, is drawn off and fed back into the continuous distillation apparatus along with the crude dicumyl peroxide feed.

By our process, high purity dicumyl peroxide is recovered from crude dicumyl peroxide mixtures not only in high purity but in high yield. The former method of simply crystallizing the dicumyl peroxide out of the crude reaction mixture left large quantities of supernatant which contained significant amounts of dicumyl peroxide. This supernatant was either discarded or further attempts were made to crystallize out the desired dicumyl peroxide product or prior art methods of distillation were carried out. In both of these methods, there is the distinct disadvantage that a number of steps are required and that the yield of pure dicumyl peroxide for each additional step is minimal. These disadvantages combine to make recovery of any additional dicumyl peroxide after the initial crystallization to be expensive, difficult, time-consuming and energy intensive. The method of our invention circumvents all of these disadvantages and allows for a rapid, easy recovery of high-purity dicumyl peroxide.

The entire scope of applicability of the present invention will become apparent from the detailed examples given hereinafter; it should be understood, however, that these specific examples, while indicating preferred embodiments of the invention, are given by way of illustration only since various changes and modifications within the spirit and scope of the invention will become apparent to those skilled in the art.

EXAMPLE I 7.3 pounds (0.2 pound-mole) of dry hydrogen chloride was introduced into 59.0 pounds (0.50 pound-mole) of alpha-methyl styrene (AMS), with agitation. This chlorinated solution was added to an additional 200.6 pounds (1.70 pound-moles) of alpha-methyl styrene, in a reaction vessel, at room temperature. To the resulting solution was added 355.6 pounds (2.00 pound-moles) of cumene hydroperoxide with about an 85% purity, with agitation. The reaction mixture was continuously agitated at a temperature range of about 35° C. to 45° C. for about eight hours. The reaction mixture was transferred to a washing tank and washed three times with 60 pound portions of an about 10% sodium hydroxide solution then once with 60 pounds of 15% sodium sulfite solution and then once with 60 pounds of 20% sodium sulfate solution plus a small amount of 5% sulfuric acid to adjust the pH to about 7. The weight of the washed crude dicumyl peroxide was 480.0 pounds. A small portion (6 pounds) of the crude product was used in the experiments described in Example II and Table I. The remainder (474 pounds) of the crude product was transferred to a vessel connected to a vacuum system and stripped under reduced pressure of 1.5–2.5 MM Hg at about 90° C. for about eight hours to remove the relatively low boiling materials. The collected mixture of low boiling materials weighed 122 pounds and the residual liquid weighed 351.5 pounds. The residue was transferred to a 55 gallon drum where it was allowed to crystallize at ambient temperature for several days then the mother liquor was removed by means of a dip stick. The filtrate weighed 136.5 pounds and was added to the washed crude dicumyl peroxide of the following run (Example III) which was carried out in the same manner as in the present run. The remaining crystalline dicumyl peroxide weighed 215.0 pounds and had a freezing point of 34.0° C. and a purity of 89.03%.

EXAMPLE II

The following experimental runs (Table I) were made to produce high purity dicumyl peroxide from the crude dicumyl peroxide produced in Example I.

This process was carried out on a laboratory scale for a total of fourteen successive runs which are summarized in the following table. It is noted that the freezing points of the products are given to show their purity. This is a rapid and reproducible means of determining the relative purity of the dicumyl peroxide—the higher the freezing point, the higher the purity. A freezing point of 32° C. is considered equivalent to a purity of about 90%.

Briefly, the runs were conducted as follows:

In run No. 1, 200 grams of crude dicumyl peroxide (DCP) was placed in a standard laboratory roto evaporator fitted with a cooling coil and with the flask placed in a hot water bath. Then 5 MM Hg of vacuum was applied with the water bath at 95° C. After 5 minutes of stripping the prepurified dicumyl peroxide, about 148.8 grams was removed from the flask and allowed to crystallize at about 10° C. The distillate, about 51.6 grams, was discarded. After crystallization and filtration, 102.6 grams of pure 90+% dicumyl peroxide was recovered along with 45.8 grams of brown filtrate or supernatant mother liquor.

EXAMPLE III

The procedure described in Example I was followed. 59.0 pounds of alpha-methyl styrene was chlorinated with 7.3 pounds of dry hydrogen chloride. The chlorinated solution was mixed with 200.6 pounds of alpha-methyl styrene in a reaction vessel. To the resulting mixture was added 355.6 pounds of cumene hydroperoxide having an 85% purity, with agitation. The agitation was continued at about 35° C. to 45° C. for eight hours. The reaction mixture was successively washed with three 60 pound portions of 10% sodium hydroxide solution, one 60 pound portion of 15% sodium sulfite solution and one 60 pound portion of 20% sodium sulfate solution containing a small amount of 5% sulfuric acid to adjust the pH to about 7.

To the washed crude product which weighed 556.0 pounds was added the 136.5 pounds of filtrate obtained from the crystallization of Example I. The resulting mixture was stripped under 1-2 mm Hg and at about 90° C. The residue weighed 606.0 pounds and was allowed to crystallize in a 55 gallon drum at ambient temperature. The crystalline dicumyl peroxide weighed 322.5 pounds and had a freezing point of 34.0° C. and a 91.30% purity. The filtrate from the crystallization weighed 283.5 pounds and was added to the washed crude dicumyl peroxide obtained from the next run which was made in the same manner as in this run.

EXAMPLE IV

Following the procedure described in Example III,

TABLE I
PURIFICATION OF DICUMYL PEROXIDE
By Stripping, Crystallization, Filtration and Recycling the Filtrate

| Run No. | Stripping Time (95° C., 5mm.) Mins. | Total Wt. of Run g. | Filtrate From Preceding Run g. | Washed Crude DCP g. | Overall Washed DCP used g. | Yield Per Wt. of Run g. | Overall Wt. of DCP Recov'd g. | FP C° | Overall Yield % Based on Washed DCP |
|---|---|---|---|---|---|---|---|---|---|
| 1 | 5 | 200.00 | 0 | 200.00 | 200.00 | 102.60 | 102.60 | 31.5 | 51.30 |
| 2 | 10 | 200.00 | 45.80 | 154.20 | 354.20 | 138.10 | 240.70 | 31.3 | 67.96 |
| 3 | 8 | 200.00 | 9.70 | 190.30 | 544.50 | 103.20 | 343.90 | 33.4 | 63.16 |
| 4 | 8 | 200.00 | 43.30 | 156.70 | 701.20 | 118.90 | 462.80 | 32.9 | 66.0 |
| 5 | 8 | 200.00 | 32.70 | 167.30 | 868.50 | 106.20 | 569.00 | 32.7 | 65.52 |
| 6 | 8 | 200.00 | 42.10 | 157.90 | 1026.40 | 104.70 | 673.70 | 32.4 | 65.64 |
| 7 | 8 | 247.50 | 47.50 | 200.00 | 1226.40 | 127.55 | 801.25 | 33.0 | 65.33 |
| 8 | 14 | 257.35 | 57.35 | 200.00 | 1426.40 | 118.05 | 919.30 | 34.6 | 64.45 |
| 9 | 15 | 276.85 | 76.85 | 200.00 | 1626.40 | 124.35 | 1043.65 | 33.3 | 64.17 |
| 10 | 15 | 289.55 | 89.55 | 200.00 | 1826.40 | 107.65 | 1151.30 | 35.0 | 63.04 |
| 11 | 18 | 320.65 | 120.65 | 200.00 | 2026.40 | 122.35 | 1273.65 | 35.0 | 62.85 |
| 12 | 20 | 336.05 | 136.05 | 200.00 | 2226.40 | 165.70 | 1439.35 | 32.8 | 64.65 |
| 13 | 20 | 316.65 | 116.05 | 200.00 | 2426.40 | 203.00 | 1642.35 | 31.8 | 67.69 |
| 14 | 20 | 313.65 | 113.65 | 200.00 | 2626.40 | 201.23 | 1843.58 | 32.2 | 70.19 |
| 15 | 40 | 112.42 | 112.42 91.00* | 0 | 2626.40 | 28.72 | 1872.30 | 33.1 | 71.29 |

* Final high-boiling brown liquid, collected after 14 runs, could not be purified any more either by stripping or by crystallization. This liquid is only 3.46% of the total weight of the total washed crude DCP product used (column 5).

NOTES
1. Based on the previous results, the washed DCP product is about 84 ± 2% of the total weight of raw materials. Therefore, the overall yield based on the total weight of raw materials is 60 ± 2% [= 71.29 × (0.84 ± 0.02)] which agrees with the laboratory results.
2. The average stripping time from these 14 runs is 12.6 minutes, 31% of the previous long stripping time for oe run (40 minutes).
3. The total weight of run (column 2) is the sum of columns 3 and 4.

In run No. 2, 154.2 grams of the crude dicumyl peroxide from Example I was added to the flask along with the 45.8 grams of filtrate from run No. 1. The conditions were maintained as for run No. 1. The stripping time was 10 minutes. The prepurified dicumyl peroxide was treated as in run No. 1, and the distillate was discarded.

The steps, as described above, were repeated fourteen times.

additional runs were made in the pilot plant. The results, shown in Table II, demonstrate that the yields generally were higher in the later runs as compared to the first few runs of each series. The lower yields of the pilot plant runs, as compared to the laboratory experiments shown in Table I, were due to mechanical losses and equipment limitations.

TABLE II

DCP PILOT PLANT PRODUCTION
By Stripping, Crystallization, Filtration and Recycling the Filtrate
For Each Run: 0.2 Mole HCL, 2.2 Moles AMS; 2.0 Moles CHP (85%); Total Weight 622.5 Lbs.

| Run No. | Total Wt. For Runs lbs. | Filtrate From Preceding Run lbs. | Washed DCP From Run lbs. | Total Washed DCP From Runs lbs. | FINAL DCP PRODUCT From Each Run lbs. | F.P. °C. | Purity % | From All Runs Wt. lbs. | Moles | Overall Yield % Based on CHP | AMS | Total Wt. |
|---|---|---|---|---|---|---|---|---|---|---|---|---|
| 1 | 622.5 | 0 | 476.5 | 476.5 | 215.0 | 34.0 | 89.03 | 215.0 | 0.80 | 40.00 | 36.36 | 34.53 |
| 2 | 1,245.0 | 134.5 | 556.0 | 1,032.5 | 322.5 | 34.0 | 91.30 | 537.0 | 1.99 | 49.75 | 45.22 | 43.17 |
| 3 | 1,867.5 | 283.5 | 554.0 | 1,586.5 | 325.0 | 34.0 | 92.11 | 862.5 | 3.19 | 53.16 | 48.33 | 46.18 |
| 4 | 2,490.0 | 351.0 | 559.0 | 2,145.5 | 239.0 | 34.0 | | 1,105.5 | 4.08 | 51.00 | 46.37 | 44.23 |
| 5 | 3,112.5 | 476.0 | 535.5 | 2,681.0 | 385.0 | 34.0 | | 1,486.5 | 5.51 | 55.10 | 50.09 | 47.75 |
| 6 | 3,735.0 | 446.0 | 546.0 | 3,227.0 | 434.0 | 34.0 | | 1,920.5 | 7.11 | 59.25 | 53.86 | 51.41 |
| 7 | 4,357.5 | 358.0 | 560.0 | 3,787.0 | 369.0 | 32.0 | | 2,289.5 | 8.48 | 60.57 | 55.06 | 52.54 |
| 8 | 4,980.0 | 333.0 | 546.0 | 4,347.0 | 358.0 | 32.0 | | 2,647.5 | 9.81 | 61.31 | 55.73 | 53.16 |
| 9 | 5,602.5 | 333.0 | 500.0 | 4,847.0 | 337.0 | 32.0 | | 2,984.5 | 11.05 | 61.38 | 55.80 | 53.27 |
| 10 | | 224.0 | | | | | | | | | | |
| | | | | | Series 2 | | | | | | | |
| 11 | 622.5 | 0 | 524.5 | 524.5 | 262.0 | 34.0 | 92.35 | 262.0 | 0.97 | 48.50 | 44.09 | 42.08 |
| 12 | 1,245.0 | 122.5 | 537.5 | 1,062.0 | 170.5 | 34.0 | | 432.5 | 1.60 | 40.00 | 36.36 | 34.73 |
| 13 | 1,867.5 | 295.0 | 554.0 | 1,616.0 | 392.0 | 31.0 | | 824.5 | 3.05 | 50.83 | 46.21 | 44.14 |
| 14 | 2,490.0 | 315.0 | 552.5 | 2,168.5 | 505.0 | 34.0 | | 1,329.5 | 4.92 | 61.50 | 55.90 | 53.39 |
| 15 | 3,112.5 | 157.0 | 577.0 | 2,745.5 | 192.0 | 32.0 | | 1,521.5 | 5.64 | 56.40 | 51.27 | 48.88 |
| 16 | 3,735.0 | 338.0 | 557.0 | 3,322.5 | 348.0 | 32.0 | | 1,869.5 | 6.92 | 57.66 | 52.42 | 50.05 |
| 17 | 4,357.5 | 453.0 | 550.0 | 3,872.5 | 484.0 | 32.0 | | 2,353.5 | 8.72 | 62.28 | 56.62 | 54.01 |
| 18 | | 326.0 | | | | | | | | | | |
| | | | | | Series 3 | | | | | | | |
| 19 | 622.5 | 0 | 505.0 | 505.0 | 223.0 | 34.0 | 94.03 | 223.0 | 0.83 | 41.50 | 37.72 | 35.82 |
| 20 | 1,245.0 | 161.5 | 544.5 | 1,049.5 | 15.5 | 34.0 | | 438.5 | 1.62 | 40.50 | 36.81 | 35.22 |
| 21 | 1,867.5 | 303.5 | 560.5 | 1,610.0 | 350.0 | 34.0 | | 788.5 | 2.92 | 48.66 | 44.24 | 42.22 |
| 22 | 2,490.0 | 295.0 | 502.5 | 2,112.5 | 375.5 | 34.0 | | 1,164.0 | 4.31 | 53.87 | 48.97 | 46.74 |
| 23 | 3,112.5 | 238.5 | 579.0 | 2,691.5 | 191.5 | 32.0 | | 1,355.5 | 5.02 | 50.20 | 45.63 | 43.55 |
| 24 | 3,735.0 | 433.0 | 595.5 | 3,287.0 | 390.0 | 32.0 | | 1,745.5 | 6.46 | 53.83 | 48.93 | 46.73 |
| 25 | 4,357.0 | 402.0 | 577.5 | 3,864.0 | 473.0 | 32.0 | | 2,218.5 | 8.22 | 57.71 | 53.37 | 50.91 |
| 26 | | 302.0 | | | | | | | | | | |
| | | | | | Series 4 | | | | | | | |
| 27 | 622.5 | 0 | 540.0 | 540.0 | 277.5 | 34.0 | | 277.0 | 1.03 | 51.50 | 46.81 | 44.57 |
| 28 | 1,245.0 | 87.5 | 565.5 | 1,104.5 | 278.0 | 34.0 | | 555.5 | 2.06 | 51.50 | 46.81 | 44.61 |
| 29 | 1,867.5 | 194.0 | 550.0 | 1,654.5 | 338.0 | 34.0 | 95.67 | 893.5 | 3.31 | 55.16 | 50.15 | 47.84 |
| 30 | 2,490.0 | 227.0 | 565.0 | 2,219.5 | 366.0 | 32.0 | | 1,259.5 | 4.66 | 58.25 | 52.95 | 50.58 |
| 31 | | 232.0 | | | | | | | | | | |

HCL = Hydrochloric Acid
AMS = Alpha-Methyl Styrene
CHP = Cumene Hydroperoxide

What is claimed is:

1. A method for purifying crude dicumyl peroxide comprising the steps of (A) rapidly distilling the crude dicumyl peroxide under vacuum and elevated temperature in a distillation apparatus to remove volatile by-products, (B) removing the distilled dicumyl peroxide from the distillation apparatus, (C) cooling the distilled dicumyl peroxide to a temperature ranging from about −10° C. to about 20° C. to crystallize dicumyl peroxide from the mixture, (D) separating and recovering the crystallized dicumyl peroxide from the supernatant liquid, (E) returning the supernatant liquid to the distillation apparatus along with additional crude dicumyl peroxide and (F) continuing the steps (A) through (E), wherein the vacuum in the distillation stage ranges from about 0.1 MM Hg absolute to about 10 MM Hg absolute, and the temperature of the crude dicumyl peroxide during the distillation stage ranges from about 85° C. to about 100° C.

* * * * *